(12) United States Patent
Gazmuri

(10) Patent No.: US 8,133,860 B2
(45) Date of Patent: *Mar. 13, 2012

(54) FACILITATION OF RESUSCITATION FROM CARDIAC ARREST BY ERYTHROPOIETIN

(75) Inventor: Raúl J. Gazmuri, Chicago, IL (US)

(73) Assignee: Rosalind Franklin University of Medicine and Science, Chicago North, IL (US)

( * ) Notice: Subject to any disclaimer, the term of this patent is extended or adjusted under 35 U.S.C. 154(b) by 731 days.

This patent is subject to a terminal disclaimer.

(21) Appl. No.: 11/489,846

(22) Filed: Jul. 20, 2006

(65) Prior Publication Data

US 2007/0021788 A1 Jan. 25, 2007

Related U.S. Application Data

(60) Provisional application No. 60/701,731, filed on Jul. 22, 2005.

(51) Int. Cl.
*A61K 38/18* (2006.01)
*A61N 1/00* (2006.01)
(52) U.S. Cl. ...... 514/7.7; 607/4; 607/5; 607/7; 514/16.4
(58) Field of Classification Search .................. None
See application file for complete search history.

(56) References Cited

U.S. PATENT DOCUMENTS

| 3,552,390 A * | 1/1971 | Muller ............................. 601/97 |
| 7,309,687 B1 * | 12/2007 | Brines et al. ....................... 514/2 |
| 2003/0104988 A1 * | 6/2003 | Brines et al. ....................... 514/8 |

OTHER PUBLICATIONS

Mitra et al. N-linked oligosaccharides as outfitters for glycoprotein folding, form and function. TRENDS in Biochemical Sciences, vol. 13 No. 3:156-163 (2006).*
Boissel et al. Erythropoietin structure-function relationships. The Journal of Biological Chemistry, vol. 268, No. 21:15983-15993 (1993).*

* cited by examiner

*Primary Examiner* — Elizabeth C Kemmerer
*Assistant Examiner* — Regina M Deberry
(74) *Attorney, Agent, or Firm* — Joseph A. Fuchs; Rockey, Depke & Lyons, LLC

(57) ABSTRACT

The present invention relates generally to the use of erythropoietin (EPO) to facilitate resuscitation from cardiac arrest. For a mammalian subject suffering from cardiac arrest, concurrent administration of EPO with resuscitation after the onset of ventricular fibrillation facilitates the resuscitation. Administration of EPO serves to attenuate myocardial abnormalities caused by cardiac arrest and the resuscitation efforts and favor improved resuscitation outcomes.

20 Claims, 3 Drawing Sheets

FACILITATION OF RESUSCITATION FROM CARDIAC ARREST BY ERYTHROPOIETIN

CROSS-REFERENCE TO RELATED APPLICATION

This application claims priority from provisional application Ser. No. 60/701,731 filed Jul. 22, 2005.

FEDERALLY SPONSORED RESEARCH OR DEVELOPMENT

Not Applicable.

BACKGROUND OF THE INVENTION

1. Field of the Invention

The present invention relates generally to the use of erythropoietin (EPO) to facilitate resuscitation from cardiac arrest. For a subject suffering from cardiac arrest, concurrent administration of EPO with resuscitation but after the onset of the cardiac arrest facilitates the resuscitation. Administration of EPO serves to attenuate myocardial abnormalities caused by cardiac arrest and the resuscitation efforts and favor improved resuscitation outcomes.

2. Background of the Invention

It is estimated that between 400,000 and 450,000 individuals suffer an episode of sudden cardiac arrest every year in the United States. Yet, the percentage of individuals who are successfully resuscitated and leave the hospital alive with intact neurological function averages less than 5% nationwide. Efforts to successfully restore life are formidably challenging. They require not only that cardiac activity be initially reestablished but that injury to vital organs be prevented or minimized. A closer examination of resuscitation statistics reveals that efficient emergency medical services (EMS) systems can initially restore cardiac activity in 30 to 40% of sudden cardiac arrest victims. Yet, nearly 40% die before admission to a hospital presumably from recurrent cardiac arrest or complications during transport. Of those admitted to a hospital, 60% die before discharge as a result of myocardial dysfunction, hypoxic brain damage, systemic inflammatory responses, intercurrent illnesses, or a combination thereof. Driving poor outcome is the severe injury that tissues suffer consequent to ischemia and reperfusion.

A cardiac arrest is the cessation of normal circulation of the blood due to failure of the ventricles of the heart to contract effectively resulting in the cessation of blood delivery to the whole body. As a consequence cells of the whole body suffer injury that result from oxygen starvation. Lack of oxygen supply to the brain causes victims to immediately lose consciousness and stop breathing. Cardiac arrest is different from a heart attack (myocardial infarction). In a cardiac arrest the heart suddenly stops beating. In a heart attack, blood flow to a region of the heart muscle is disrupted. That region of the heart muscle deprived of blood flow suffers injury which might lead to cell death if blood flow is not restored promptly. During a heart attack, only a part of the heart ceases to work properly; the rest of the heart muscle continues to work promoting blood flow albeit the total work produced by the heart may be sometimes diminished. However, heart attacks can sometimes lead to cardiac arrest in which the heart as whole stops beating and ceases to promote blood flow into the systemic circulation (as described above).

In apparently healthy adults, cardiac arrest is often precipitated by ventricular fibrillation. Ventricular fibrillation most often occurs associated with underlying coronary artery disease. In this setting, ventricular fibrillation may be the initial manifestation of a heart attack. However, ventricular fibrillation may also occur not associated with a heart attack but associated with electrical abnormalities of the heart muscle originating in a region of the heart in which there is reduction of blood flow or disproportionate increase in oxygen demands in such region. Ventricular fibrillation can also occur associated with trauma to the heart; associated with diseases that affect the heart muscle itself such cardiomyopathies; associated with congenital or acquired abnormalities of ion channels that regulate the way in which the electrical impulse of the heart is initiated and propagated; associated with the administration of drugs that can alter such ion channels; associated with abnormalities in the chemical composition of the blood that can alter the way in which the electrical impulse of the heart is initiated and propagated; and associated with abnormalities in the valves of the heart. Cardiac arrest can also occur without ventricular fibrillation, case in which the heart stops beating because of asystole in which there is no electrical impulses originating from the heart, or because of pulseless electrical activity in which electrical impulses originating from the heart are not effective to promote normal contraction of the heart muscle. Cardiac arrest caused by asystole or pulseless electrical activity is typically associated with conditions leading to severe curtailment of the amount of oxygen delivered to the heart muscle, which can occur associated with respiratory failure or severe loss of circulating blood volume. Cardiac arrest caused by asystole or pulseless electrical activity can also occur associated with existing cardiac disease, especially when severe heart failure has developed.

In children, cardiac arrest is more commonly caused by severe curtailment of oxygen delivery to the heart muscle, which can occur associated with near-drowning or respiratory failure. However, children can also suffer cardiac arrest caused by ventricular fibrillation.

After onset of cardiac arrest, profound global myocardial ischemia develops. The ensuing resuscitation efforts promote flow across the ischemic myocardium, which—albeit obligatory for resuscitation—creates conditions for reperfusion injury. As a consequence several functional myocardial abnormalities develop during cardiac arrest and the resuscitation efforts that in of itself can compromise the capability for reestablishing cardiac activity. These abnormalities include the development of ischemic contracture during cardiac resuscitation that manifests by left ventricular wall thickening with reductions in cavity size and that limits forward blood flow generation by chest compression. Early after return of spontaneous cardiac activity, there is prominent ventricular ectopic activity with frequent episodes of refibrillation. In addition, systolic and diastolic left ventricular function is reversibly impaired causing variable degrees of hemodynamic dysfunction. We have previously shown that these myocardial abnormalities can be ameliorated by inhibition of the sodium-hydrogen exchanger isoform-1 (NHE-1) using cariporide (Ayoub I M, Kolarova J D, Yi Z, Trevedi A, Deshmukh H, Lubell D L, Franz M R, Maldonado F A, Gazmuri R J. Sodium-hydrogen exchange inhibition during ventricular fibrillation: Beneficial effects on ischemic contracture, action potential duration, reperfusion arrhythmias, myocardial function, and resuscitability. *Circulation* 2003; 107:1804-1809: Gazmuri R J, Ayoub I M, Hoffner E, Kolarova J D. Successful ventricular defibrillation by the selective sodium-hydrogen exchanger isoform-1 inhibitor cariporide. *Circulation* 2001; 104:234-239; Gazmuri R J, Hoffner E, Kalcheim J, Ho H, Patel M, Ayoub I M, Epstein M, Kingston S, Han Y. Myocardial protection during ventricular fibrillation by reduction of proton-driven sarcolemmal sodium influx. *J Lab Clin Med* 2001; 137:43-55; Kolarova J D, Ayoub I M, Gazmuri R J. Kolarova J D, Ayoub I M, Gazmuri R J. Cariporide enables hemodynamically more effective chest compression by leftward shift of its flow-depth relationship. *Am J Physiol Heart Circ Physiol* 2005; 288:H2904-H2911; Kolarova J, Yi Z, Ayoub I M, Gazmuri R J. Cariporide potentiates the effects of epinephrine and vasopressin by nonvascular mechanisms during closed-chest resuscitation. *Chest* 2005; 127:1327-1334).

The present invention discloses that administration of the glycoprotein hormone erythropoietin (EPO) also serves to attenuate these myocardial abnormalities and favor improved resuscitation. EPO has been traditionally viewed as a primary regulator of red blood cell production (Graber S E, Krantz S B. Erythropoietin and the control of red cell production. *Annu Rev Med* 1978; 29:51-66). Yet, recent studies demonstrate the EPO also exerts protective effects on the myocardium in the setting of ischemia and reperfusion injury (Cai Z, Manalo D J, Wei G, Rodriguez E R, Fox-Talbot K, Lu H, Zweier J L, Semenza G L. Hearts from rodents exposed to intermittent hypoxia or erythropoietin are protected against ischemia-reperfusion injury. *Circulation* 2003; 108:79-85; Calvillo L, Latini R, Kajstura J, Leri A, Anversa P, Ghezzi P, Salio M, Cerami A, Brines M. Recombinant human erythropoietin protects the myocardium from ischemia-reperfusion injury and promotes beneficial remodeling. *Proc Natl Acad Sci USA* 2003; 100:4802-4806; Tramontano A F, Muniyappa R, Black A D, Blendea M C, Cohen I, Deng L, Sowers J R, Cutaia M V, El Sherif N. Erythropoietin protects cardiac myocytes from hypoxia-induced apoptosis through an Akt-dependent pathway. *Biochem Biophys Res Commun* 2003; 308:990-994; Cai Z, Semenza G L. Phosphatidylinositol-3-kinase signaling is required for erythropoietin-mediated acute protection against myocardial ischemia/reperfusion injury. *Circulation* 2004; 109:2050-2053; Lipsic E, van der Meer P, Henning R H, Suurmeijer A J H, Boddeus K M, van Veldhuisen D J, van Gilst W H, Schoemaker R G. Timing of erythropoietin treatment for cardioprotection in ischemia/reperfusion; United States Patent Application Pub. No. 2004/0009908A1; United States Patent Application Pub. No. 2004/0198663A1; United States Patent Application Pub. No. 2005/0075287; International Patent Application WO 03/057242; International Patent Application No. WO 2004/00464). In a rat model of myocardial infarction caused by left anterior descending coronary artery (LAD) occlusion and reperfusion, administration of recombinant human erythropoietin (rhEPO) attenuated post infarct deterioration in hemodynamic function by reduction of cardiomyocyte loss, attenuated the reactive hypertrophy of surviving cardiomyocytes, and also prevented apoptosis (Moon C, Krawczyk M, Ahn D, Ahmet I, Paik D, Lakatta E G, Talan M I. Erythropoietin reduces myocardial infarction and left ventricular functional decline after coronary artery ligation in rats. *Proc Natl Acad Sci USA* 2003; 100:11612-11617).

These and other aspects and attributes of the present invention will be discussed with reference to the following drawings and accompanying specification.

BRIEF SUMMARY OF THE INVENTION

In an embodiment, the present invention discloses a method for facilitating cardiac resuscitation in a mammalian subject suffering from cardiac arrest comprising administration of an effective amount of erythropoietin (EPO), or its derivative, or a functional fragment thereof, to the subject concurrent with cardiac resuscitation and after the onset of cardiac arrest. In a preferred embodiment, the mammalian subject is human. In another preferred embodiment, the EPO is a recombinant human EPO (rhEPO). The effective amount of EPO can be from about 200 U/kg to about 6,000 U/kg, and preferably 5,000 U/kg.

The cardiac resuscitation in the present invention can be mechanical, electrical, chemical, or a combination thereof. The cardiac resuscitation can also be closed-chest or open-chest.

The EPO can be administered by a route selected from, but is not limited to, intravenous (IV), intraarterial (IA), intraperitoneal (IP), intracardiac (IC), and intraosseous (IO). The administration can be bolus or continuous.

The EPO, or its derivative, or a functional fragment thereof, can be administered just immediately before cardiac resuscitation, at the beginning of the cardiac resuscitation, or during cardiac resuscitation. In an embodiment, the cardiac arrest is due to ventricular fibrillation.

DETAILED DESCRIPTION OF THE INVENTION

Figure 1:
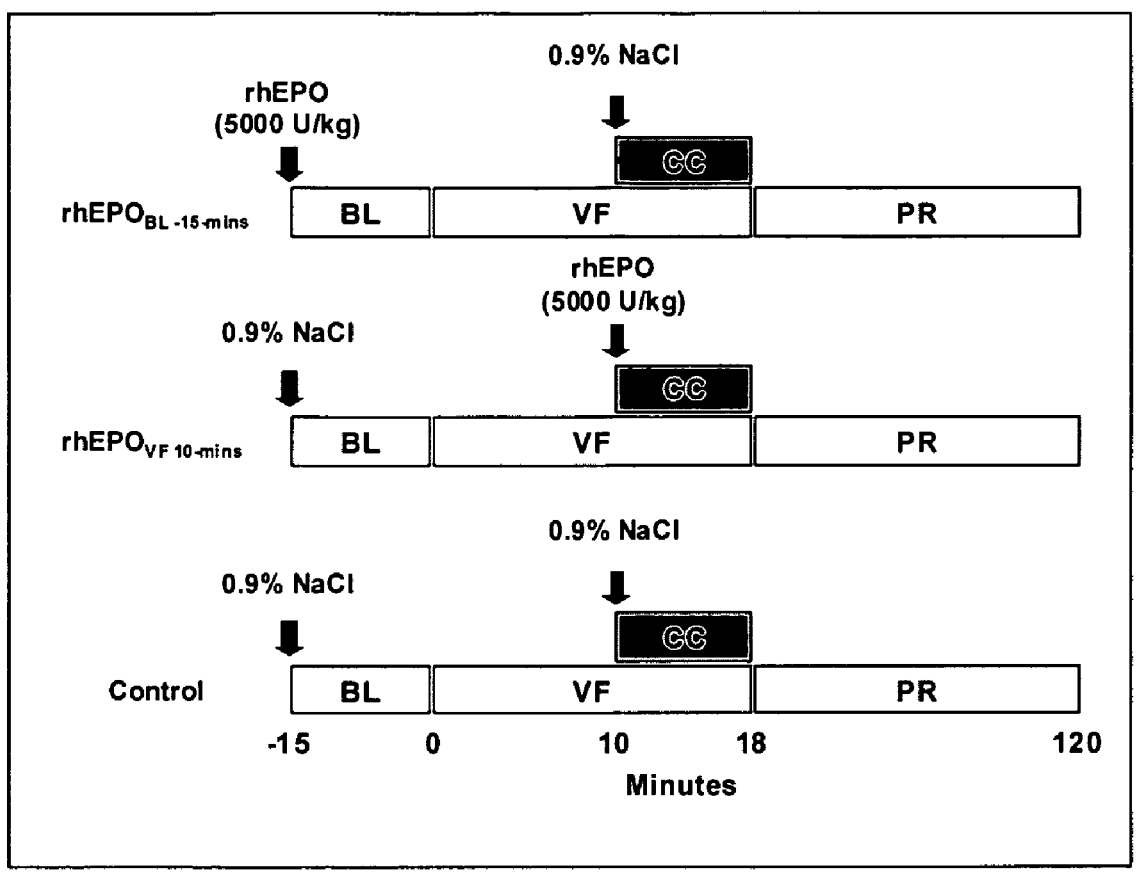
FIG. 1 is a schematic diagram showing the study design for the present invention using a rat model of ventricular fibrillation (BL=baseline, VF=ventricular fibrillation, and CC=chess compression). With the investigators blind to the assignment, rats were randomized to receive a right atrial bolus of rhEPO (5000 U/kg) at baseline 15 minutes before induction of VF (rhEPO$_{BL\ -15\text{-}min}$), at 10 minutes of VF immediately before starting chest compression (rhEPO$_{VF\ 10\text{-}min}$), or 0.9% NaCl solution (control)

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

The present invention relates generally to the use of erythropoietin (EPO) to facilitate resuscitation from cardiac arrest. For a mammalian subject suffering from cardiac arrest, concurrent administration of EPO with resuscitation facilitates the resuscitation. Administration of EPO serves to attenuate myocardial abnormalities caused by cardiac arrest and the resuscitation efforts and favor improved resuscitation outcomes. Without being bound by any one or more specific theories, the improved resuscitation outcomes may be explained by one or more of the following hypotheses:

1. Administration of EPO during cardiac arrest and resuscitation prevents the development of ischemic contracture, facilitates electrical defibrillation, promotes post-resuscitation electrical stability, ameliorates post-resuscitation myocardial dysfunction, and improves short-term survival.
2. The treatment effect of EPO increases as the severity of ischemic injury increases (e.g., as a result of prolonging the duration of untreated ventricular fibrillation).

We have conducted studies to investigate in a rat model of ventricular fibrillation whether EPO could facilitate resuscitation from cardiac arrest.

Study Design

These studies were conducted in a rat model of ventricular fibrillation and closed-chest resuscitation to assess the effects of the interventions (in this case, the intervention is the administration of EPO) on the hemodynamic efficacy of chest compression, resuscitability, post-resuscitation ectopic activity, post-resuscitation myocardial function, and short-term survival.

The ventricular fibrillation model is significantly different than the coronary occlusion models used by others in studying cardioprotection from ischemia and reperfusion injury. In the ventricular fibrillation model used in the present disclosure, ventricular fibrillation is induced by delivering a 60-Hz alternating current to the right ventricular endocardium. This, results in cessation of the organized activity of the heart required for effective work as a pump leading to cessation of blood flow. The myocardial ischemia induced by ventricular fibrillation is global (throughout the entire heart). The ventricular fibrillation model is best suited for studying cardiac arrest. In the occlusion model, a coronary artery is ligated to reduce or stop blood flow to the heart to induce myocardial infarction (MI). Ischemia induced by occlusion of the coronary artery is occurring in only part of the heart, not the entire myocardium. The occlusion model is best suited for studying acute coronary syndromes. In the ventricular fibrillation model, the heart suddenly stops beating. This is different from a heart attack in the occlusion model in which blood flow to the heart is disrupted to the point that part of the heart muscle dies but the rest continues to function promoting systemic blood flow. Coronary occlusion, however, can sometimes lead to cardiac arrest. In the ventricular fibrillation model the heart suffers intense ischemia because in addition to cessation of blood supply, the metabolic needs of the heart muscle are increased by the fibrillatory activity. In addition, because the duration of the episode of myocardial ischemia is much shorter in the ventricular fibrillation model than in the occlusion model (i.e., 5, 8, or 10 minutes vs 30, 45, or 60 minutes) before reperfusion, the main abnormality in the ventricular fibrillation model is that of dysfunction whereas in the coronary occlusion model the main abnormality is that of cell death. The main therapeutic goal in the ventricular fibrillation model is the prevention of cell dysfunction; whereas the main therapeutic goal in the coronary occlusion model is the prevention of cell death. In addition, the ventricular fibrillation model is accompanied by whole body ischemia and responses that are unique to the cardiac arrest setting that can also influences the heart. Thus, the same benefit produced by EPO in the heart may apply to other organs including the brain during cardiac arrest.

The study design is shown schematically in FIG. 1. Ventricular fibrillation was left untreated for 10 minutes. Chest compression was then started and defibrillation attempted 8 minutes later (at ventricular fibrillation 18 minutes). Three groups of eight rats each were randomized to receive (a) rhEPO (EPOGEN®, Amgen Inc., Thousand Oaks, Calif., USA) in bolus dose of 5000 IU/kg into the right atrium at 15 minutes before induction of ventricular fibrillation and equal volume of 0.9% NaCl at 10 minutes of untreated VF immediately before start of chest compression ($rhEPO_{BL\ -15\text{-}min}$), (b) 0.9% NaCl at 15 minutes before induction of VF and rhEPO 5000 IU/kg at 10 minutes of untreated VF immediately before starting chest compression ($rhEPO_{BL\ 10\text{-}min}$), and (c) 0.9% NaCl at 15 minutes before induction of VF and at 10 minutes of untreated VF (Control). The investigators were blind to the treatment assignment.

The rhEPO dose was chosen empirically based on previous reports in which doses ranging between 1000 U/kg to 5000 U/kg were used intraperitoneally (Cai Z, Manalo D J, Wei G, Rodriguez E R, Fox-Talbot K, Lu H, Zweier J L, Semenza G L. Hearts from rodents exposed to intermittent hypoxia or erythropoietin are protected against ischemia-reperfusion injury. *Circulation* 2003; 108:79-85; Calvillo L, Latini R, Kajstura J, Leri A, Anversa P, Ghezzi P, Salio M, Cerami A, Brines M. Recombinant human erythropoietin protects the myocardium from ischemia-reperfusion injury and promotes beneficial remodeling. *Proc Natl Acad Sci USA* 2003; 100: 4802-4806; Tramontano A F, Muniyappa R, Black A D, Blendea M C, Cohen I, Deng L, Sowers J R, Cutaia M V, El Sherif N. Erythropoietin protects cardiac myocytes from hypoxia-induced apoptosis through an Akt-dependent pathway. *Biochem Biophys Res Commun* 2003; 308:990-994; Moon C, Krawczyk M, Ahn D, Ahmet I, Paik D, Lakatta E G, Talan M I. Erythropoietin reduces myocardial infarction and left ventricular functional decline after coronary artery ligation in rats. *Proc Natl Acad Sci USA* 2003; 100:11612-11617), one study in which a dose of 300 U/kg was used intravenously (Abdelrahlnan M, Sharples E J, McDonald M C, Collin M, Patel N S, Yaqoob M M, Thiemermann C. Erythropoietin attenuates the tissue injury associated with hemorrhagic shock and myocardial ischemia. *Shock* 2004; 22:63-69), and one study in an isolated rat heart preparation in which the heart was exposed to 10 U/ml. (Wright G L, Hanlon P, Amin K, Steenbergen C, Murphy E, Arcasoy M O. Erythropoietin receptor expression in adult rat cardiomyocytes is associated with an acute cardioprotective effect for recombinant erythropoietin during ischemia-reperfusion injury. *FASEB J* 2004; 18:1031-1033). Given that the volume of distribution of rhEPO has been reported to range between 0.021 L/kg to 0.61 L/kg (Lim V S, DeGowin R L, Zavala D, Kirchner P T, Abels R, Perry P, Fangman J. Recombinant human erythropoietin treatment in pre-dialysis patients. A double-blind placebo-controlled trial. *Ann Intern Med* 1989; 110:108-114; Macdougall I C, Roberts D E, Neubert P, Dharmasena A D, Coles G A, Williams J D. Pharmacokinetics of recombinant human erythropoietin in patients on continuous ambulatory peritoneal dialysis. *Lancet* 1989; 1:425-427), in a 500 g rat the volume of distribution would range from ≈10 to 300 ml. Thus, to attain a plasma concentration of 10 U/ml (as in the isolated rat heart study), the total amount of rhEPO required would range from ≈100 to 3000 U corresponding to a single dose of 200 to 6000 U/kg. Given no expected adverse effects, we chose the upper range and selected a dose of 5000 U/kg. Yet, a few pilot studies (i.e., 2 rats) were conducted to assess for hemodynamic effects during spontaneous circulation in our model. The formulation of rhEPO used in these experiments was 4000 U/ml. Thus, the volume of rhEPO and 0.9% NaCl (control) to be administered was 1.25 ml/kg. rhEPO was kept refrigerated at 4° C. and warmed to room temperature before use. This dose of rhEPO would not be expected to increase the hematocrit but to have an effect during the episode of resuscitation and the subsequent post-resuscitation interval. During an observation period of 120 minutes post-resuscitation, no change in hematocrit relative to control rats occurred.

Methods

Animal Preparation

Sprague-Dawley rats (450-550 g) were anesthetized by intraperitoneal injection of sodium pentobarbital (45 mg/kg) and supplemented with 10 mg/kg at 30-minute intervals. Core temperature was maintained between 36.5° C. and 37.5° C. using an infrared heating lamp. A 5F catheter was orally advanced into the trachea and used subsequently for mechanical ventilation. Proper placement was verified with an infrared $CO_2$ analyzer (CO2SMO model 7100, Novametrix Medical Systems, Inc). A conventional lead II electrocardiogram was recorded through subcutaneous needles. Through the left femoral vein, a PE50 catheter was advanced into the right atrium for measurement of right atrial pressure. Through the right femoral artery, a PE50 catheter was advanced into the abdominal aorta for aortic pressure measurements and blood sampling. Through the left femoral artery, a thermocouple microprobe (IT-18, Physitemp) was advanced to measure cardiac output by thermodilution technique. Through the left jugular vein, a PE50 catheter was advanced into the right atrium for bolus injection of 0.9% NaCl for cardiac output measurement. In addition, a precurved guide was advanced into the right atrium through the right jugular vein and was used for induction of ventricular fibrillation.

Experimental Protocol

Ventricular fibrillation was induced by delivering a 60-Hz alternating current to the right ventricular endocardium and left untreated for a predetermined interval. Chest compression was then initiated using an electronically controlled and pneumatically driven (50 PSI) chest compressor (CJ-80623, CJ Enterprises) programmed to deliver 200 compressions per minute. The depth of compression was adjusted within the initial two minutes to attain an aortic diastolic pressure between 26 and 28 mmHg and thus secure a coronary perfusion pressure above the resuscitability threshold of 20 mmHg in rats. The location and depth of compression were adjusted if required to secure that the coronary perfusion pressure remained within the target range throughout chest compression. The depth of compression was continuously measured using a displacement transducer. Positive pressure ventilation was concomitantly provided with a volume controlled ventilator (model 683, Harvard Apparatus) programmed to deliver 25 unsynchronized breaths per minute using 100% oxygen. Defibrillation was attempted after 8 minutes of chest compression by delivering a maximum of two 3-J transthoracic shocks using a biphasic waveform defibrillator (Smart Biphasic Heartstream XL M4735A, Agilent Technologies). If ventricular fibrillation persisted or an organized rhythm with a mean aortic pressure of $\leq 25$ mmHg ensued, chest compression was resumed for 30 seconds. The defibrillation-compression cycle was repeated for up to three additional times, increasing the energy of individual shocks (if ventricular fibrillation persisted) to 5-J and then to 7-J for the last two cycles. Successful cardiac resuscitation was defined as the return of an organized electrical activity with a mean aortic pressure $\geq 60$ mmHg for $\geq 5$ minutes. Successfully resuscitated rats were monitored for 120 minutes. At the end of 120 minutes euthanasia was performed by intravenous injection of sodium pentobarbital (150 mg/kg). These procedures were consistent with the recommendations of the Panel on Euthanasia of the American Veterinarian Medical Association. Autopsy was performed opening the thoracic and abdominal cavity. Organs were inspected for evidence of traumatic injury related to vascular catheterization and chest compression.

Measurements and Data Analysis

Analog signals were processed using BIOPAC signal-conditioners (BIOPAC Systems, Inc) and digitized at 250 scans/second using a 16-bit data acquisition board (AT-MIO-16XE-50, National Instruments). The signals were displayed, stored, and analyzed using programs written for Lab VIEW 4.01 (National Instruments). Vascular pressures were measured using fluid-filled catheters and conventional pressure transducers referenced to mid-chest level. Coronary perfusion pressure was calculated as the aortic minus the right atrial pressure at the end of chest relaxation during chest compression. Cardiac output was measured after bolus injection of 200-µL of 0.9% NaCl at room temperature into the right atrium. The dilution curves were analyzed using custom-developed LabVIEW-based software.

Statistical Methods

The data were analyzed using SigmaStat™ for Windows. ANOVA with multicomparison procedures used to test for differences among groups at specific time intervals. Comparable non-parametric tests were substituted when tests for normality and equal variance failed. A p-value of <0.05 was considered statistically significant.

Results

Figure 2:
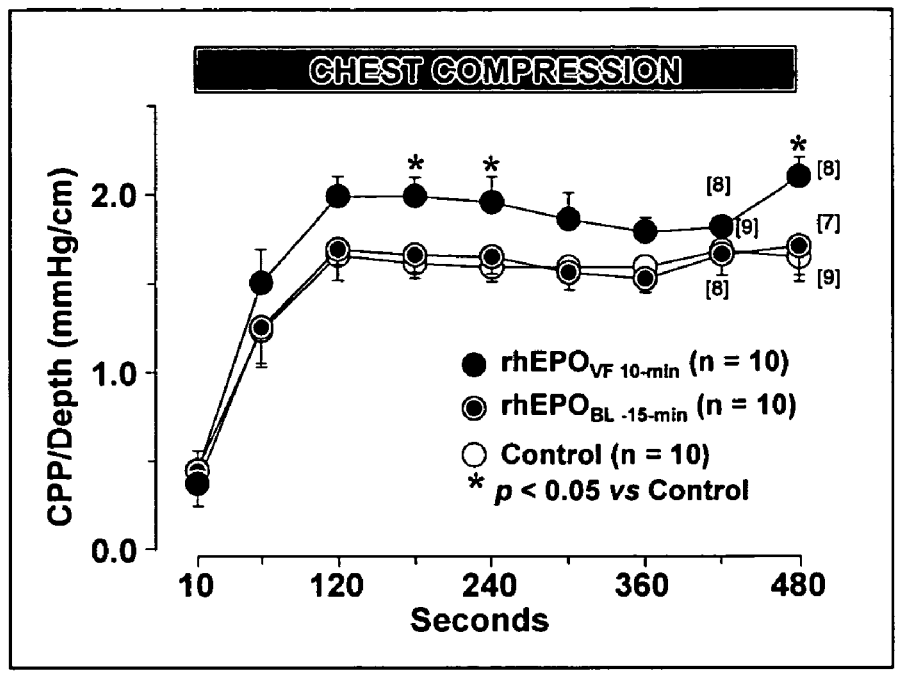
FIG. 2 shows the ratio between coronary perfusion pressure (CPP) and depth of compression during closed-chest resuscitation in rats treated with human recombinant EPO (rhEPO) as shown in FIG. 1 and described below in the text. Rats that received rhEPO had a significantly higher CPP/depth ratio during chest compression indicative that rhEPO attenuated the development of ischemic contracture and enhanced the hemodynamic efficacy of closed-chest resuscitation.
Figure 3:
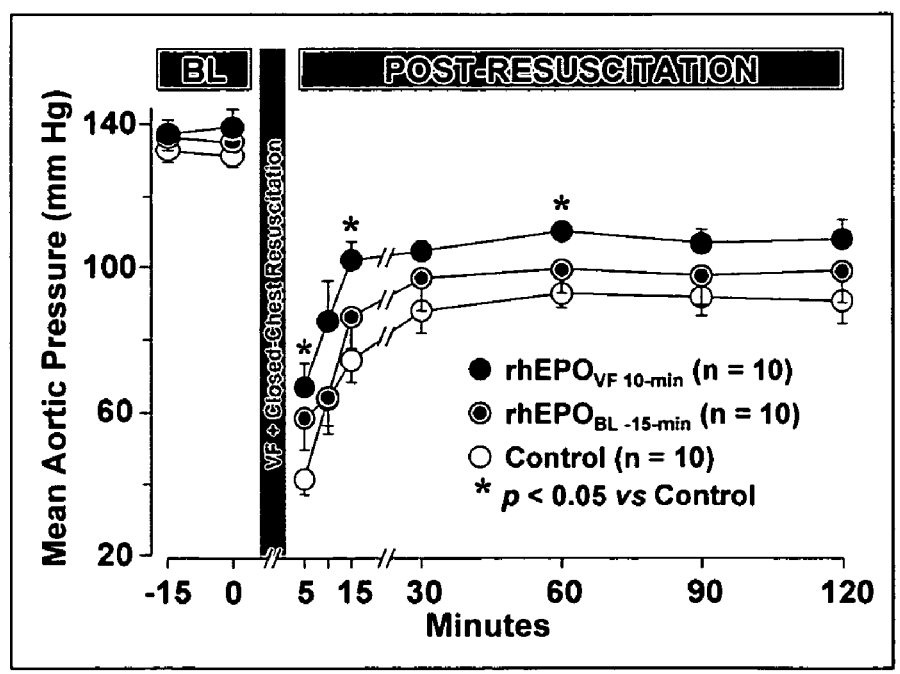
FIG. 3 shows the mean aortic pressure after return of spontaneous circulation in rats treated with rhEPO as described in the text.
Figure 4:
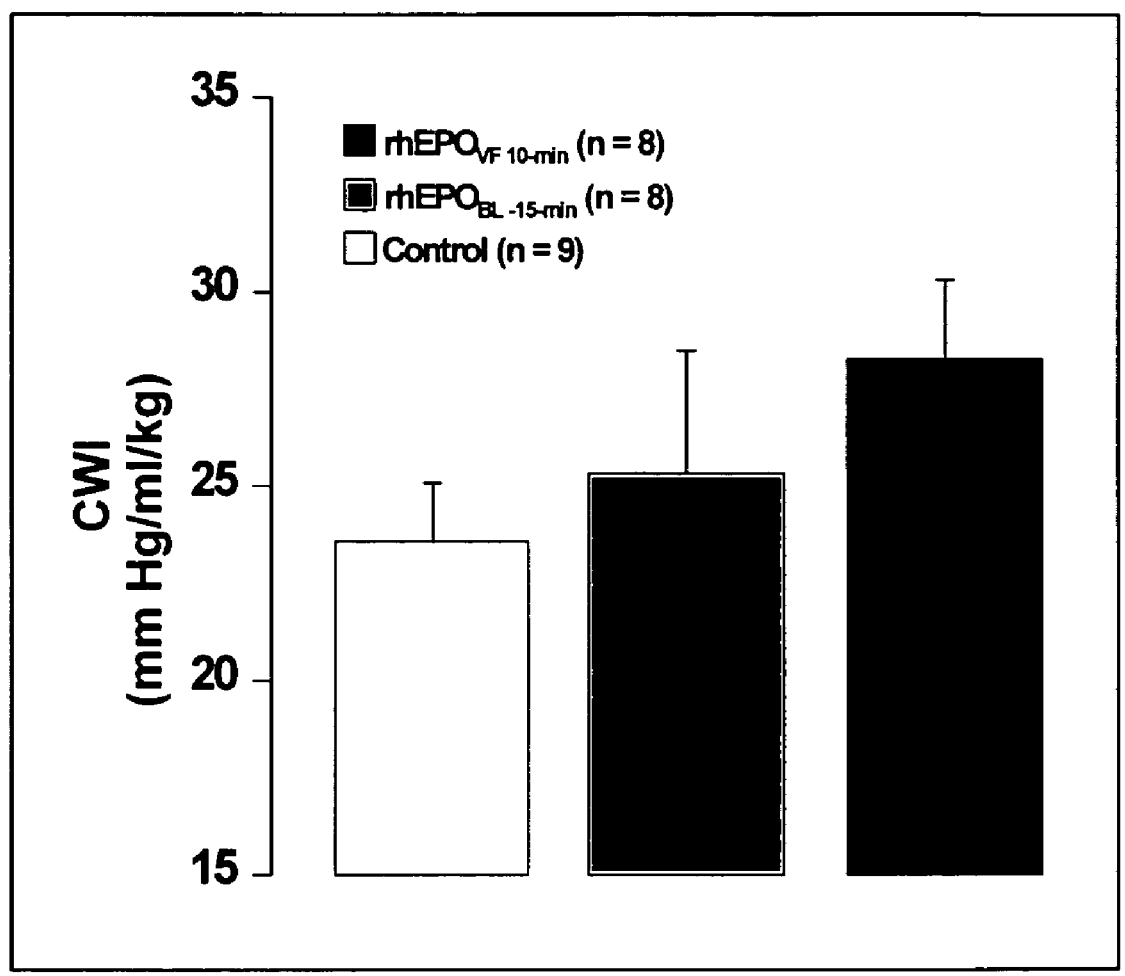
FIG. 4 shows the cardiac work index (CWI) averaged from post-resuscitation minute 10 to post-resuscitation minute 120 in rats treated with rhEPO. CWI was calculated as the difference between the mean aortic and mean right atrial pressure times the stroke volume index.

The results are summarized in FIGS. 2, 3, and 4. rhEPO given at the time of VF—but not at baseline—promoted hemodynamically more effective chest compression such that the ratio between the coronary perfusion pressure (CPP) and the depth of compression averaged during the interval of chest compression was $1.95 \pm 0.27$ in $rhEPO_{VF\ 10-min}$, $1.63 \pm 0.23$ in $rhEPO_{BL\ -15-min}$, and $1.62 \pm 0.26$ mmHg/mm in control groups (p<0.05 $rhEPO_{VF\ 10-min}$ vs $rhEPO_{BL\ 15-min}$ and control). FIG. 2 depicts the CPP/depth ratio over time during chest compression. Post-resuscitation, $rhEPO_{VF\ 10-min}$ rats had significantly higher mean aortic pressure than control rats (FIG. 3). Cardiac work calculated as the difference between the mean aortic and mean right atrial pressure times the stroke volume index was numerically higher in $rhEPO_{VF\ 10-min}$ rats than in $rhEPO_{BL\ -15-min}$ rat and than control rats (FIG. 4).

From the studies disclosed in the present application, it is evident that concurrent administration of an effective amount of EPO is effective in facilitating the resuscitation of a mammalian subject suffering from cardiac arrest when the EPO is administered concurrent with resuscitation and after the onset of the cardiac arrest. In a preferred embodiment, the mammalian subject is human. In another preferred embodiment, the cardiac arrest is due to ventricular fibrillation.

What is meant by "facilitating the resuscitation" in the present disclosure is an improvement of the resuscitation outcome by promoting hemodynamically more effective resuscitation such as, but is not limited to, an increase in the ratio between the coronary perfusion pressure (CPP) and the depth of compression or ensuring better hemodynamic function post-resuscitation in which there is higher mean aortic pressure and cardiac work index. "Facilitating the resuscitation" can also be measured by other methods such as, but are not limited to, an improvement on the rate on initial resuscitation, and an improvement on the rate of survival of the subject.

What is meant by "concurrent" is that the EPO is administered at any time during the resuscitation, including any time just immediately before cardiac resuscitation to the completion of the resuscitation procedure. In an embodiment, the EPO is administered just immediately before cardiac resuscitation. In another embodiment, the EPO is administered at the beginning of the resuscitation. In yet another embodiment, the EPO is administered during the cardiac resuscitation, which is any time between after the beginning of the resuscitation and before the end of the resuscitation procedure.

Though rhEPO was used in the present study, other forms of erythropoietin can be used in the place of rhEPO, which include but are not limited to any variants, fragments, conjugates, derivatives, and mutants of the erythropoietin protein, produced by natural, recombinant or synthetic means. The forms of erythropoietin (which is used interchangeably in the present invention with EPO) that can be used in the present invention include but are not limited to: naturally-occurring, synthetic and recombinant forms of erythropoietin from human or other mammalian species, as well as other erythropoietin-related molecules. The term erythropoietin or EPO, therefore, includes any molecule which possesses erythropoietin activities similar to those found in the naturally-occurring human erythropoietin or any molecule that stimulates erythropoietin activities, which includes but is not limited to: erythropoietin, asialoerythropoietin, deglycosylated erythropoietin, erythropoietin analogs, erythropoietin mimetics, erythropoietin fragments, hybrid erythropoietin molecules, erythropoietin receptor-binding molecules, erythropoietin agonists, renal erythropoietin, brain erythropoietin, oligomers and multimers thereof, muteins thereof, and congeners thereof. The examples of the various forms of erythropoietin or EPO listed above also embrace the variants in the extents of and sites of glycosylation.

What is meant by "an effective amount" of EPO is a dose of EPO from about 200 to about 6,000 U/kg. In a preferred embodiment, the effective amount is about 5,000 U/kg.

In the example above, the EPO was administered in bolus dose into the right atrium. However, EPO can also be administered by other routes, such as, but not limited to, intravenous (IV), intraarterial (IA), intraperitoneal (IP), intracardiac (IC), and intraosseous (IO). In a preferred embodiment, EPO is administered intraosseously. The administration can be in bolus or can be continuous. Formulation of the EPO will vary according to the route of administration selected. An appropriate formulation comprising EPO to be administered can be prepared in a physiologically acceptable vehicle or carrier and optional additional ingredients. "Acceptable vehicle or carrier" includes but is not limited to any and all solvents, dispersion media, antibacterial and antifungal agents, isotonic agents, and the like which are compatible with the activity of the EPO and are physiologically acceptable to the subject. "Additional ingredients" include, but are not limited to, one or more of the acceptable pharmaceutical excipients, which are well known to those skilled in the art in formulation.

As shown in our studies, one single dose of EPO is enough to accomplish the facilitation of cardiac resuscitation in the present disclosure.

"Resuscitation" in the present invention, also referred to as "cardiac resuscitation", includes one or more procedures to restore the pumping function of the heart, which may include but are not limited to mechanical or electrical procedures, or by chemical means (e.g., administration of epinephrine). A common mechanical procedure is cardiac compression by rhythmically pressing on the chess of the subject. The procedure can be performed manually by a person or by the use of a mechanical or electromechanical device. Cardiac resuscitation by cardiac compression is often accompanied by efforts to maintain oxygenation by artificially maintaining the breathing function of the lungs. This combined procedure is known as "cardiopulmonary resuscitation" or CPR in brief. An example of an electrical procedure is the use of a defibrillator in which electrical shocks are applied for the purpose of ending ventricular fibrillation. Resuscitation can be performed with the chest closed or the chest open.

As mentioned earlier, the administration of EPO is concurrent with the resuscitation efforts. What is meant by "concurrent" is that the EPO is administered immediately before, at the beginning of, or during the resuscitation efforts but after the onset of cardiac arrest, and ventricular fibrillation in particular. Our data indicate that administration of EPO before ventricular fibrillation is less effective.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

I claim:

1. A method for preserving left ventricular myocardial distensibility during cardiopulmonary resuscitation whereby the hemodynamic efficacy of chest compression improves in a mammalian subject suffering from cardiac arrest comprising administration of an effective amount of erythropoietin (EPO), wherein the EPO is wildtype or recombinant wildtype EPO, to the subject concurrent with cardiac resuscitation to increase the ratio of coronary perfusion pressure (CPP) to depth of chest compression.

2. The method of claim 1, wherein the mammalian subject is human.

3. The method of claim 1, wherein the EPO is a recombinant human EPO (rhEPO).

4. The method of claim 1, wherein the effective amount of EPO is from about 200 U/kg to about 6,000 U/kg.

5. The method of claim 1, wherein the effective amount of EPO is about 5,000 U/kg.

6. The method of claim 1, wherein the cardiac resuscitation is mechanical, electrical, chemical, or a combination thereof.

7. The method of claim 1, wherein the cardiac resuscitation is closed-chest or open-chest.

8. The method of claim 1, wherein the EPO is administered by a route selected from the group consisting of: intravenous (IV), intraarterial (IA), intraperitoneal (IP), intracardiac (IC), and intraosseous (10).

9. The method of claim 1, wherein the administration of EPO is in bolus or continuous.

10. The method of claim 1, wherein the cardiac arrest is due to ventricular fibrillation, pulseless electrical activity, or asystole.

11. A method for preserving left ventricular myocardial distensibility during cardiopulmonary resuscitation whereby the hemodynamic efficacy of chest compression improves in a mammalian subject suffering from cardiac arrest comprising administration of an effective amount of erythropoietin (EPO), wherein the EPO is wildtype or recombinant wildtype EPO, to the subject concurrent with cardiac resuscitation at a time between the onset of cardiac arrest and post resuscitation to increase the ratio of coronary perfusion pressure (CPP) to depth of chest compression.

12. The method of claim 11, wherein the mammalian subject is human.

13. The method of claim 11, wherein the EPO is a recombinant human EPO (rhEPO).

14. The method of claim 11, wherein the effective amount of EPO is from about 200 U/kg to about 6,000 U/kg.

15. The method of claim 11, wherein the effective amount of EPO is about 5,000 U/kg.

16. The method of claim 11, wherein the cardiac resuscitation is mechanical, electrical, chemical, or a combination thereof.

17. The method of claim 11, wherein the cardiac resuscitation is closed-chest or open-chest.

18. The method of claim 11, wherein the EPO is administered by a route selected from the group consisting of: intravenous (IV), intraarterial (IA), intraperitoneal (IP), intracardiac (IC), and intraosseous (IO).

19. The method of claim 11, wherein the administration of EPO is in bolus or continuous.

20. The method of claim 11, wherein the cardiac arrest is due to ventricular fibrillation, pulseless electrical activity, or asystole.

* * * * *